United States Patent [19]

Matsutani et al.

[11] Patent Number: 5,775,902
[45] Date of Patent: Jul. 7, 1998

[54] ROOT CANAL TREATMENT INSTRUMENT AND MANUFACTURING METHOD FOR THE ROOT CANAL TREATMENT INSTRUMENT

[75] Inventors: Kanji Matsutani; Hiroshi Hirano; Katsutoshi Satoh; Takayuki Matsumoto, all of Tochigi-ken, Japan

[73] Assignee: Kabushiki Kaisha Matsutani Seiskusho, Shioya-gun, Japan

[21] Appl. No.: 577,330

[22] Filed: Dec. 22, 1995

[30] Foreign Application Priority Data

Dec. 27, 1994 [JP] Japan .................................. 6-324163

[51] Int. Cl.$^6$ ............................................. A61C 1/02
[52] U.S. Cl. ............................................. 433/102; 433/224
[58] Field of Search ..................... 433/81, 102, 141, 433/164, 165, 224; 606/80; 604/95

[56] References Cited

U.S. PATENT DOCUMENTS

| | | | |
|---|---|---|---|
| 3,660,901 | 5/1972 | Inoue | 433/102 |
| 3,751,176 | 8/1973 | Von Hollen | 433/165 |
| 3,916,529 | 11/1975 | Mousseau | 433/224 |
| 4,925,445 | 5/1990 | Sakamoto et al. | 604/95 |
| 5,069,226 | 12/1991 | Yamauchi et al. | 604/95 |
| 5,125,838 | 6/1992 | Seigneurin | 433/102 |
| 5,243,996 | 9/1993 | Hall | 604/281 |
| 5,380,200 | 1/1995 | Heath et al. | 433/102 |
| 5,464,362 | 11/1995 | Heath et al. | 433/102 |
| 5,498,158 | 3/1996 | Wong | 433/102 |
| 5,503,554 | 4/1996 | Schoeffel | 433/102 |
| 5,628,674 | 5/1997 | Heath et al. | 433/102 |

OTHER PUBLICATIONS

Walia et al, *An Initial Investigation of the Bending and Torsional Properites of Nitinol Root Canal Files*, Journal of Endotonics, vol. 14, No. 7, Jul. 1988, pp. 346–351.

*Primary Examiner*—Ralph Lewis
*Attorney, Agent, or Firm*—Townsend&Banta

[57] ABSTRACT

This invention relates to a root canal treatment instrument comprising: a needle extending in a rodlike form, comprising: working section made of a superelastic alloy extending from a distal end of the needle; and a shank extending axially between the working section and a proximal end of the needle, made of at least partially a non-superelastic alloy, and a handle attached to a proximal end of the needle and adapted to be manipulated by a hand of a dentist. The working section possesses flexible nature because of its superelastic alloy composition, whereas the shank possesses rigid nature because of its non-superelastic alloy composition.

4 Claims, 3 Drawing Sheets

ROOT CANAL TREATMENT INSTRUMENT AND MANUFACTURING METHOD FOR THE ROOT CANAL TREATMENT INSTRUMENT

BACKGROUND OF THE INVENTION

1. Field of the Invention

This invention relates to a root canal treatment instrument for endodontic treatments and a manufacturing method for the root canal treatment instrument.

2. Description of Prior Art

As instruments used for treatments of tooth root canals, reamers and files for drilling and finishing the root canals, compactors, fillers, spreaders, and pluggers for filling thermoplastic resin into the root canal, cleansers for removing residuals in the root canal, broaches for filling cotton in the root canal, and the like, are known. Such a root canal treatment instrument or endodontic instrument is formed either with a working section constituted of cutting blades, barbs on a shaft, or the like corresponding to its treatment purpose formed on a fine shank member or with a member having a work section formed of a spiral shank. Some instrument has a handle attached unitedly to the end of the member to be controlled by a dentist's hand, one in the form of a hand piece to be chucked thereto, or a shank portion to be directly manipulated by the dentist.

The shape and diameter of the root canal is diverse, generally very fine, and greatly depending on individuals. The intercanal instrument therefore needs, even if made of a single type, many models having different sizes. When the canal is operated by drilling of such as a reamer, the reamer is required to be transformed to extend along the shape of the root canal so as to avoid to sustain damages on the walls of the canal. In other words, the root canal instrument must have a proper elasity.

A conventional root canal instrument, uses, as a forming material, a linear material made of stainless steel, is constituted by forming a working section in a predetermined range from the tip of the linear material and by attaching a handle for manipulation to the other end of the linear material, and displays the diameter difference in the same type instrument by coloring at a predetermined position thereof.

It is to be noted that the ISO standard defines the relationship between the diameter of the root canal instrument and the color.

Since the shape of the root canal is diverse and so depending on individuals, there raises a problem that it is difficult to accurately estimate working length up to the apical end of the root from a radiograph taken for the treatment. To solve such a problem, an estimation of the working length up to the apex by electrical measurement is performed as described in Japanese Utility Model Publication No. Hei 6-26.257.

Such a conventional root canal treatment instrument is constituted of stainless steel having proper rigidity and elasity. However, to treat a bending root canal in which the bending degree thereof tends to vary person by person, there is a demand to develop a root canal treatment instrument having high restorability and flexibility. A root canal treatment instrument used for a technique disclosed in the Japanese Utility Model Publication No. Hei 6-26.257 is for one manipulated by a dentist's hand. Thus, there is a demand to develop a root canal treatment instrument capable of estimating the working length while it is chucked to the hand piece or the like. Moreover, when the root canal is operated, light may be reflected on the surface of the stainless steel, causing a problem that the area to be treated cannot be seen well.

SUMMARY OF THE INVENTION

It is an object of the invention to provide a root canal treatment instrument having high restorability and flexibility and a manufacturing method thereof.

It is another object of the invention to provide a root canal treatment instrument capable of being manipulated well in an area of limited space during the treatment, being readily recognized, and working for estimation of the intercanal working length by electrical conduction while chucked on a hand piece.

The foregoing objects are accomplished with a root canal treatment instrument including a needle extending in a rodlike form, and a handle attached to a proximal end of the needle and adapted to be manipulated by a dentist's hand. The needle has a working section made of a superelastic alloy extending from a distal end of the needle, and a shank extending axially between the working section and a proximal end of the needle, made of at least partially a non-superelastic alloy portion. The working section possesses flexible nature because of its superelastic alloy composition, whereas the shank possesses rigid nature because of its non-superelastic alloy composition. The dentist can conduct a good operation by bending only the working section even when the area to be treated is a narrow, limited area such as of a molar.

In accordance with an embodiment of the invention, at least a part of the working section or the shank is colored differently from the natural color of the superelastic alloy. The root canal treatment instrument can therefore be easily distinguished from one made of stainless steel. The instrument may be given one of multiple colors so as to render distinction of diameter thereof easier. Such coloring may reduce the light reflection during the operation and render the root canal treatment instrument recognized easily by the dentist, thereby rendering the operation easier.

The shank of the needle can be fitted into a hole formed in the handle, which is made of either a metal or a synthetic resin, and be securely coupled to the hole by an anaerobic adhesive, thereby improving concentricity between the needle and the handle. Therefore, no eccentric rotation may occur even where the instrument is attached to a rotary drive device such as a hand piece. The handle may be formed of a conductive material and be electrically connected to the needle to allow the electrical current to flow between the handle and the needle. When the handle is attached to the rotary drive apparatus, the hand piece is connected to a human body through the handle and the needle. As a result, the working length up to the apical end of the root can be readily estimated by measuring the resistance where the electrical current flows between the handle and the human body.

A manufacturing method for the root canal treatment apparatus according to the invention, includes the steps of preparing a superelastic alloy as an original material, forming the working section by removing process of the superelastic alloy, and providing memorizing thermal treatment to the superelastic alloy. Either of the removing process and the memorizing thermal treatment can precede one another. When the removing process is subsequent to the memorizing thermal treatment, the superelastic alloy is maintained at the temperature for the memorizing treatment or less during the removing process.

The removing process may include a step of forming a taper on the working section and a step of forming flutes on the working section, one step of which may precede another step, to reduce increment of the temperature accompanied with the forming processes to maintain memorizing effects by the thermal treatment. Accordingly, the working section of the root canal treatment instrument such as a reamer, a file, or the like, can be formed in a tapered shape with helical flutes in maintaining superelasity.

BRIEF DESCRIPTION OF THE DRAWINGS

The above and other objects and features of the invention are apparent to those skilled in the art from the following preferred embodiments thereof when considered in conjunction with the accompanied drawings, in which.

DETAILED DESCRIPTION OF THE PREFERRED EMBODIMENTS

Figure 1:
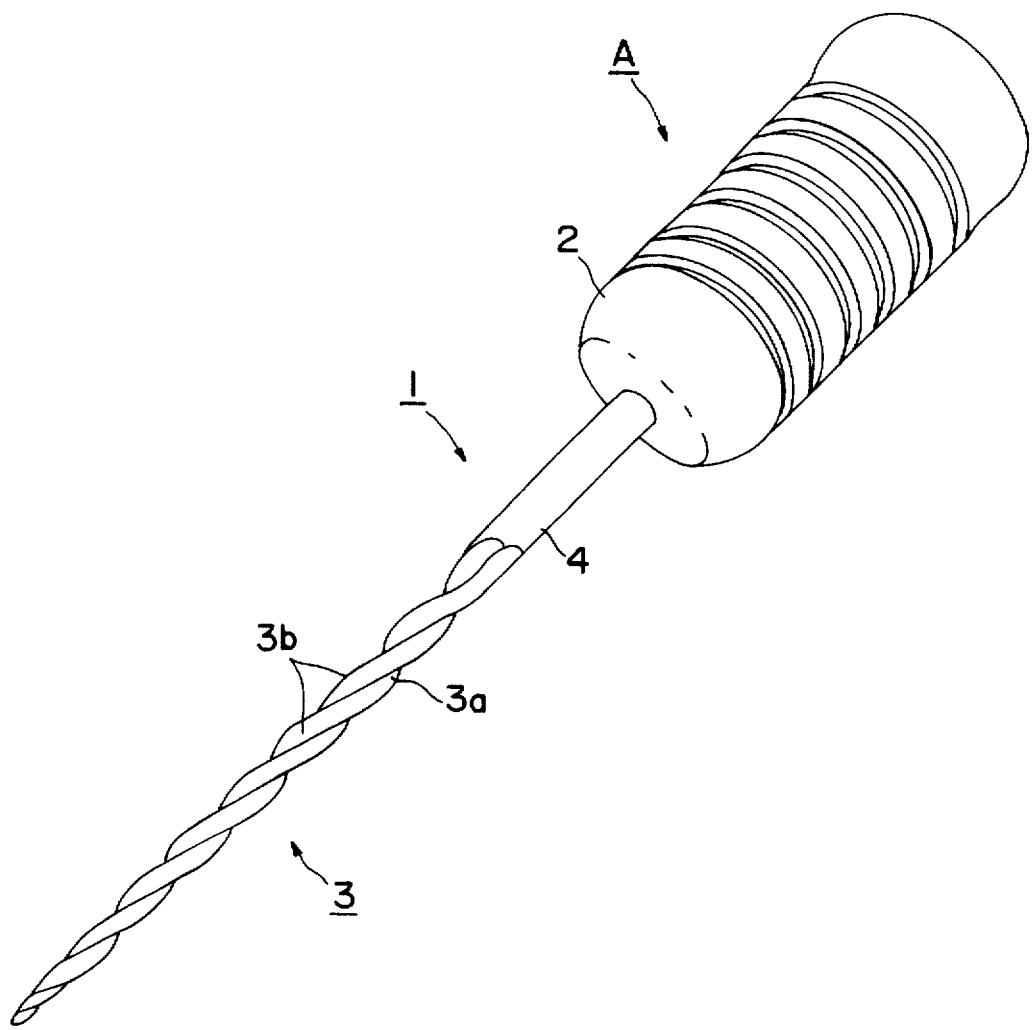
FIG. 1 is a perspective view of a reamer of a preferred embodiment according to the invention.

Referring to the drawings in detail, in particular, to FIG. 1, a reamer A, a typical root canal treatment instrument, is shown. It is to be noted that this invention for a root canal treatment instrument can apply to any endodontic instrument, or intercanal instrument.

FIG. 1 shows the shape of the reamer A. The reamer A is an instrument for drilling the inner walls of the root canal and is constituted of a needle 1 made of a superelastic alloy and a handle 2 attached to a proximal end of the needle 1. A tapered working section 3 is formed at the needle 1 from the tip of the needle 1 for a predetermined length, and the rest of the needle 1 serves as a part of a shank 4 extending axially. The working section 3 is formed with helical flutes 3a and cutting blades 3b extending along the flutes 3a. The handle 2 is made of a synthetic resin or a metal such as stainless steel, and is attached to the shank 4 of the needle 1. When the handle 2 is made of the synthetic resin, the needle 1 can be inserted into the handle 2 and molded to form both in a united body; when the handle 2 is made of the metal or even the synthetic resin, the handle 2 can be formed with a hole, not shown, and the needle 1 can be put into the hole and secured by an anaerobic adhesive.

With the reamer A thus formed, a dentist holds the handle 2 thereof and inserts the working section 3 into a root canal of a tooth to be operated, and then moves the reamer A in an axial direction thereof in rotating in the cutting direction of the cutting blades 3b, thereby enabling to drill the inner walls of the root canal to finish the root canal. It is to be noted that the working section 3 is not necessarily formed with the cutting blades 3b in other root canal treatment instrument except the reamer, and can be formed in a coil shape with a taper or barbs. The handle 2 is not necessarily made of the synthetic resin, and can be made of a metal such as stainless steel, or can be made, without having a united body, to be chucked at every time when used.

The needle 1 is made of the superelastic alloy, formed in a shape of the aimed instrument, and provided with a memorizing thermal treatment so that in the range of normal temperature the needle 1 performs with superelasity. Accordingly, the needle 1 is extremely flexible and has high restorability. In an endodontic operation, the root canal treatment instrument according to the invention is therefore highly applicable to any canal shapes which may vary person by person. It is known that when the needle is rotated while the needle is bent, the needle receives fatigue due to repetitive bending and may reach a breakdown. The needle 1 made of the superelastic alloy has a high resistance against the fatigue due to such repetitive bending, is very durable, and therefore enables itself to be attached to a rotary drive device such as a hand piece to operate in rotating with a high speed.

The inventors of the invention have conducted a comparative experiment for durability of the needles of a #25 reamer (its material diameter 0.6 millimeter), made of a superelastic alloy and a stainless steel. In this experiment, the respective needles are attached to the hand piece to be projected 25 millimeters from a chucking unit; their projecting portions are passed respectively through a stainless pipe having an inner diameter of 0.82 millimeter bent by 60 degrees at a position 12 millimeters away from the end; the respective needles are rotated with 125 r.p.m., and time and rotation number when the respective needles reach the breakdown is measured. Each needle had three samples.

In the results of this experiment, regarding the needle 1 made of the superelastic alloy, the mean time to reach the breakdown was 2 minutes 31 seconds, and the rotation number was 314 rounds at that time. To the contrary, regarding the needle made of stainless steel, the mean time to reach the breakdown was only 10 seconds, and the rotation number was 12 rounds at that time. The results of the experiment imply that the root canal treatment can be accelerated if a dentist uses a rotary drive device such as a hand piece with the root canal treatment instrument having the needle made of the superelastic alloy. Consequently, with the root canal treatment instrument, a treatment method can be effectuated in which the treatment time for a patient is so shortened and which the patient feels more painless.

Figure 2A:
FIGS. 2(a) to 2(c) are diagrams showing processes for manufacturing the reamer according to the invention.
Figure 2B:
Figure 2C:
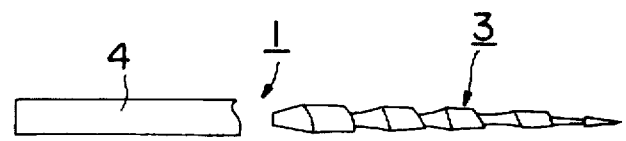

Referring to FIG. 2, a manufacturing method for such a reamer A is shown. The needle 1 forming the reamer A is made from a linear material of the superelastic alloy. In this embodiment, a nickel-titanium alloy is used as the superelastic alloy; the superelastic alloy is wire-withdrawn to form a linear material with its diameter corresponding to the needle 1 of the wanted reamer A; and the linear material is cut by a predetermined length to achieve an original material 11 as shown in FIG. 2(a). The original material 11 has a diameter determined stepwise between 0.4 and 1.8 millimeter so as to correspond types of the reamer A to be manufactured. When the needle 1 of the reamer A is constituted from the original material 11, a range corresponding to the length of the working section 3 from one end of the original material 11 is sharpened into a taper as shown in FIG. 2(b), and then, as shown in FIG. 2(c), flutes 3a are ground to form cutting blades 3b. The needle 1 corresponding to the aimed reamer A can be manufactured from the original material 11 by such taper and flute fabrications. It is to be noted that the order between the taper fabrication and the flute fabrication with respect to the original material 11 are not restricted to the one described above, and the identical needle 1 can be manufactured by conducting a taper fabrication subsequent to the flute fabrication. By conducting the taper fabrication and the flute fabrication as the different processes, the processing amount, or a drilled or ground amount, with respect to the original material 11 can be reduced per one fabrication process, so that the heat occurrence due to the fabrications can be reduced.

When the needle 1 is formed from the original material 11, the aimed needle 1 can be manufactured by a taper fabrication and a flute fabrication by means of grinding after a predetermined shape (i.e., a straight shape in the reamer A) is memorized in the original material 11 by processing memorizing thermal treatment. In addition, before the original material 11 is subject to the memorizing thermal treatment process, the taper and flute fabrications as well as other fabrication, for example such as, a pressing process for forming a stopper on the shank 4 to prevent the shank 4 from being pulled out when the needle 1 and handle 2 are assembled unitedly, can be made, and then the needle 1 that has completed other prescribed processes can be subject to the memorizing thermal treatment process.

When the original material 11 is a nickel-titanium alloy, the memorizing thermal treatment process can be conducted by holding the original material 11 in a shape into which memorization is produced, or in a straight shape in the reamer A, by heating the material 11 at 400 to 500 degree Celsius, and by maintaining the heated material 11 for certain hour. After the memorizing process is made at the temperature above, the formative memorization can be erased by heating the material 11 at about 600 degree Celsius. Accordingly, after the memorizing thermal treatment process is made, when the needle 1 is manufactured by providing the taper and flute fabrications, it is required to strictly manage the temperature so that the original material 11 is never heated at 600 degree Celsius or more during the fabrications. The heat generation accompanied by the fabrications of the original material 11 may be reduced by conducting the fabrications as the separated processes, thereby enabling the original material 11 to be prevented from increasing the temperature thereof Such temperature management may also be implemented by sufficient fluid for grinding to cool the material 11 during the fabrications. When the needle 1 is manufactured by providing the taper and flute fabrications to the original material 11 prior to the memorizing thermal treatment, it would be unnecessary to strictly manage the temperature of the original material 11 during the fabrications. After fabricated, the original material 11 is held in a straight shape and then subjected to the memorizing thermal treatment, thereby forming the needle 1 with the superelastic nature.

In this embodiment, the formative restoring temperature of the needle 1 is designed at about zero degree Celsius and constituted to demonstrate the superelasity at the normal temperature. When the reamer A is employed, the needle 1 maintains its straight shape as a normal memorization shape and transforms itself very easily and smoothly along the inner walls of the root canal as inserted into the root canal, thereby enabling a dentist to finish the root canal according to dentist's manipulation for rotation or reciprocal movement in the axial direction of the needle 1. When the inner wall of the root canal is finished, the needle 1 is able to flexibly transform itself according to external force exerting thereto, so that the needle 1 does not grind unnecessarily the inner walls of the canal, and so that a good finished shape is obtainable. The needle 1 makes the treatment easier than that using the conventional root canal treatment instrument having a stainless steel needle. When the needle 1 is disengaged from the root canal upon the completion of working in the root canal, the external force that had exerted to the needle 1 disappears, and the needle 1 restores its straight shape as the original memorized shape.

In this invention, the sequence between the memorizing thermal treatment process for the original material 11 and the fabrications of the taper and flutes conducted by grinding, is not limited and determined based on shapes of the reamer A and other endodontic instruments and on restrictions from fabrication processes. As described above, the needle 1 of the aimed root canal treatment instrument as typified by the reamer A can be constituted either by fabricating the taper and flutes in managing the temperature for the original material 11 after the original material 11 consisted of the superelastic alloy is subject to the memorizing thermal treatment process or by processing the memorizing thermal treatment after the taper and flutes are fabricated to form a prescribed shape prior to the memorizing thermal treatment process.

Figure 3:
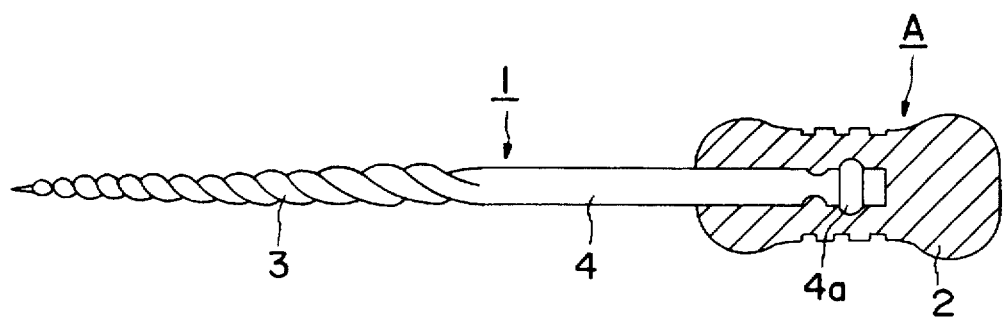
FIG. 3 is a cross section showing an attachment structure of the needle and handle of the reamer.

When the handle 2 is unitedly formed on the shank 4 formed as a part of the needle 1 by injection molding, it is preferable, as shown in FIG. 3, to form a stopper 4a by plastic working either in a shape expansively made from a part of the shank 4 or in a shape flatly transformed from a part of the shank 4, to avoid the handle 2 to disengage the shank 4 after the needle 1 is formed in particular during an endodontic treatment. It is however required that the shank 4 does not have the superelastic ability when the shank 4 is subject to the plastic working.

Figure 4:
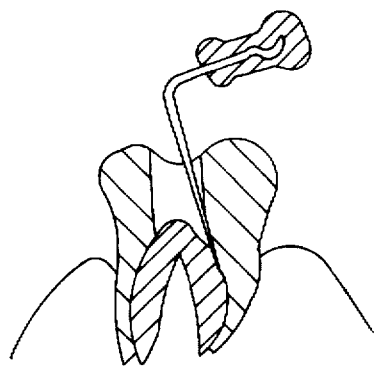
FIG. 4 is an illustration showing a shape of the needle when a molar is treated.

When the root canal of the molar is treated by the reamer A, the space in which the reamer A is manipulated is narrow and makes the manipulation of the reamer A inconvenient. In such a situation, as shown in FIG. 4, the needle 1 may be bent midway of the needle 1 to direct only the working section 3 located at the tip of the needle 1 to the molar and inserted into the root canal, and the reamer A may be pushed and pulled in the axial direction without rotating the reamer A to finish the root canal. When such operation is to be conducted, the shank 4 cannot be maintained in a form that the shank 4 is bent midway if the needle 1 has the superelastic ability across the whole length. To satisfy the conditions above, the reamer A according to the embodiment is constituted so that a part or all of the shank 4 forming the needle 1 does not indicate the superelasity. That is, all or a part of the shank 4 does not have the superelasity but has the eigen-elasity from the material, and the shank 4 is constituted so as to be capable of conducting plastic transformation. Even if all or a part of the shank 4 of the needle 1 thus has the eigen-elasity from the material, the portion inserted into the canal when the root canal is treated is the working section 3, so that the durability of the needle 1 against repetitive bending accompanied with the rotation of the needle 1 can be sufficiently ensured.

To fabricate the needle 1 so that the working section 3 in the needle 1 maintains or is provided with its superelasity and so that at all or a part of the shank 4 of the needle 1 its superelasity is erased or stayed away from application of the superelasity, all or a part corresponding to the shank 4 may be partially heated at 600 degree Celsius or more to increase the temperature of the shank 4 to erase the formative memorization if the original material 11 has already been subject to the memorizing thermal treatment, or all or a part corresponding to the shank 4 may remain as it is if the original material is not yet subject to the memorizing thermal treatment.

As described above, all or a part of the shank 4 is constituted so as not to have the superelasity, so that the stopper 4a can be formed by providing the plastic working at a position corresponding to the stopper 4a of the shank 4. The handle 2 can be integrated as a united body with the end on the shank's side of the needle 1 by the insert molding where the shank 4 is formed with the stopper 4a. Even if the dentist treats an area extremely less manipulative such as a molar, the manipulatability can be improved by bending the shank 4 at a desirable position.

In this embodiment, the reamer can be distinguished from other reamers by giving either or both of the working section 3 and the shank 4 of the needle 1 of the reamer A the different color from the original color of the superelastic material. One of the reasons to distinguish a particular reamer from other reamers is the differences of materials forming the reamers. That is, reamers and other endodontic instruments are generally made of the stainless steel these days. If the reamer made of the stainless steel is compared with the reamer made of the superelastic alloy, the dentist who manipulates the reamer feels the reamers differently when the root canal is finished. Therefore, if the reamer made of the stainless steel and the reamer made of the superelastic alloy are juxtaposed on a table, the dentist is required to distinguish those reamers. In particular, the reamer A has variations of 14 types, the diameter of the tip between 0.08 and 0.8 millimeter, length of 0.02 millimeter, 0.05 millimeter, and 0.1 millimeter. The ISO standard set colors corresponding to the respective types, and generally, such coloring is made on the handle 2 to distinguish the types.

By coloring either or both of the working section 3 and at least a part of the shank 4 of the needle 1 of the reamer A differently from the original color of the superelastic material, the reamer can be distinguished from other reamers made of the stainless steel which have the color in the original material. To apply or produce a color different from the original material color to the needle 1 made of the nickel-titanium alloy, there are methods to adjust the atmosphere when the memorizing thermal treatment is conducted, to use an anode oxidation process, or the like. In the method in which the atmosphere when the memorizing thermal treatment is conducted is adjusted, whether the color is made on the needle 1 or not can be selected by conducting the memorizing thermal treatment in the air atmosphere or the non-oxide atmosphere. If the color is made, the color density of the needle 1 can be changed according to the amount containing the oxygen. Thus, at least a part of the needle 1 is colored differently from the original material color, so that the reamer made of the superelastic alloy can be clearly distinguished from reamers made of stainless steel and other endodontic instruments. In the anode oxidation method, multiple colors different from each other can be produced by changing the bias voltage. In this method, by producing multiple colors (for example, fourteen different colors) clearly distinguishable from each other corresponding to the diameter of the needle 1, the types corresponding to the diameters can be clearly distinguished from each other based on the color of the needle 1 in addition to the coloring on the basis of the types given by the ISO standard. In sum, the reamer A made of the superelastic alloy and the reamer made of the stainless steel can be clearly distinguished from one another, and the types corresponding to the diameters in the reamer A can be also clearly distinguished.

In the reamer A according to the invention, the synthetic resin handle 2 is integrated by the insert molding with the end of the shank 4 of the needle 1. However, as an instrument for treatment, other constitution may be used; for example, a handle 2 as a single piece is made by injection molding of a synthetic resin or by machinery fabrication of a metal, and the shank 4 is fitted into the handle 2 and is coupled with the handle 2 by an anaerobic adhesive. The root canal treatment instrument, after used, is subject to sterilization using heat or agent. The adhesive must be selected so as to endure a certain temperature. Accordingly, if made of the metal, the handle 2 may not be impaired even in association with the sterilization, so that the handle 2 can be used for a long time repetitively.

Figure 5:
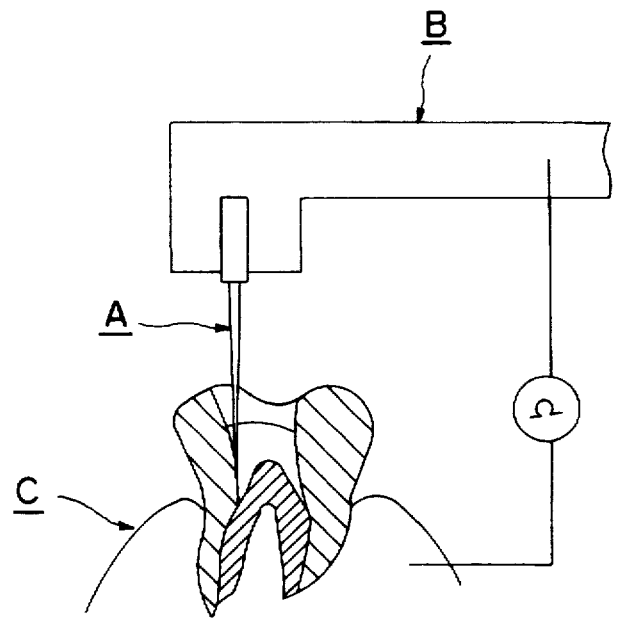
FIG. 5 is an illustration showing a method for measuring resistance to estimate a working length for endodontic treatment.

When the handle 2 is made of a metal, the reamer A may become conductive. As shown in FIG. 5, therefore, the working length can be estimated by measuring the change of resistance where an electric current is flown between the hand piece B attaching the reamer A and the human body C, thereby enabling the dentist to easily work on the root canal.

When the reamer A is constituted by making the handle 2 and the needle 1 adhere, the concentricity between the handle 2 and the needle 1 can be improved. Consequently, even when the reamer A is rotated with a high speed, centrifugal force due to possible eccentricity may not exert, and therefore, finishing the root canal can be conducted under a desirable situation. For example, in the case that a dentist manipulates the reamer A by his hand, the workability may not be impaired even if the handle 2 and the needle 1 lack the concentricity therebetween. However, when the reamer A is rotated with a high speed, the needle 1 is rotated eccentrically if lacking the concentricity, so that vibrations may be transmitted to the dentist who is manipulating the hand piece to disturb the controllability of the hand piece, and so that the shape of the root canal may be worse.

Some adhesive used for coupling the handle 2 with the needle 1 may disturb the conduction between the handle 2 and the needle 1 by encroachment of liquid film of the adhesive into a tiny gap formed between the handle 2 and needle 1. However, if the anaerobic adhesive is used, such disturbance may not occur, so that the handle 2 and the needle 1 can maintain the conductivity therebetween.

As described above, in the manufacturing method for the root canal treatment instrument according to the invention, the root canal treatment instrument having the superelasity can be formed either by the taper and flute fabrications in which the original material is subject to the removing process such as grinding or the like where the superelastic alloy material that has been subjected to the memorizing thermal treatment process is maintained at a temperature of the memorizing thermal treatment or less, or by the memorizing thermal treatment process after the original material is subject to the removing process prior to the memorizing thermal treatment.

The root canal treatment instrument is very flexible such that the instrument smoothly transforms itself according to external force slightly exerted thereto and bends back to the memorized shape quickly upon a release from the external force. Therefore, the instrument will not exert excessive force to the inner walls of the root canal when the root canal is finished, so that a good root canal operation can be implemented easily.

With the root canal treatment instrument according to the invention, since at least a part of the shank has a portion of non-superelasity, the stopper for engagement with the handle can be formed at the portion, and when the handle is formed by the insert molding unitedly with the needle, the shank and the handle can be engaged firmly. When the tooth to be treated is located around an area having a limited access thereto as of a molar, only the shank is bent and inserted easily into the root canal.

Since either or both of the working section and at least a part of the shank of the root canal treatment instrument is colored differently from the original color of the raw material, the root canal treatment instrument can be clearly distinguished from other root canal treatment instrument made of the stainless steel having the same function. When multiple colors different from each other are produced, the types set according to the diameters thereof can be distinguished.

The root canal treatment instrument manipulated by a hand or the rotary drive device such as the hand piece can be constituted by forming the handle as a single piece made of the synthetic resin or the metal and then by engaging the handle with the shank and making them adhere with the anaerobic adhesive. The root canal instrument can flow a current between the instrument and the human body when the root canal is operated by connecting the needle and handle electrically. Therefore, the root canal treatment instrument will assist the estimation of the working length by monitoring the resistance and makes the root canal operation easier.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not to be limited by the specification, but be defined by the claims set forth below.

What is claimed is:

1. A root canal treatment instrument comprising:
   an elongated cylindrical needle having a proximal end and a distal end;
   a working section made of a super-elastic alloy extending from said distal end of the needle; and
   a shank extending axially between the working section and said proximal end of the needle;
   a transformed portion formed on said shank which does not have super-elastic ability; and
   a handle attached to said proximal end of the needle so as to cover said transformed portion.

2. The root canal treatment instrument as set forth in claim 1, wherein the handle is made of a metal or a synthetic resin, and wherein the shank is securely engaged to a hole formed in the handle by an anaerobic adhesive.

3. The root canal treatment instrument as set forth in claim 1, wherein the handle is conductive, and wherein the needle is electrically connected to the handle.

4. The root canal treatment instrument as set forth in claim 1, wherein the superelastic alloy is made by wire-withdrawal, wherein the working section is formed by removal of the original material, and wherein a portion of the needle has a color different from the natural color of the superelastic alloy.

* * * * *